(12) United States Patent
Kanngiesser

(10) Patent No.: US 6,893,398 B2
(45) Date of Patent: May 17, 2005

(54) DEVICE FOR MEASURING INTRAOCULAR PRESSURE, IN PARTICULAR A TONOMETER

(75) Inventor: Hartmut Kanngiesser, Zurich (CH)

(73) Assignee: ODC Ophthalmic Development Company AG, Zurich (CH)

( * ) Notice: Subject to any disclaimer, the term of this patent is extended or adjusted under 35 U.S.C. 154(b) by 0 days.

(21) Appl. No.: 10/125,546

(22) Filed: Apr. 19, 2002

(65) Prior Publication Data

US 2002/0159031 A1 Oct. 31, 2002

(30) Foreign Application Priority Data

Apr. 19, 2001 (CH) ............................................. 0710/01
Aug. 28, 2001 (EP) ............................................. 01810832

(51) Int. Cl.[7] ............................................. A61B 3/16
(52) U.S. Cl. .................................. 600/399; 600/405
(58) Field of Search ................................ 600/398, 399, 600/405, 406, 587, 561

(56) References Cited

U.S. PATENT DOCUMENTS

| | | | |
|---|---|---|---|
| 4,089,329 A | | 5/1978 | Couvillon et al. |
| 4,305,399 A | * | 12/1981 | Beale .................... 600/398 |
| 4,922,913 A | | 5/1990 | Waters, Jr. et al. |
| 4,922,914 A | | 5/1990 | Segal et al. |
| 5,032,020 A | | 7/1991 | Robert |
| 5,217,015 A | | 6/1993 | Kaye et al. |
| 5,501,217 A | * | 3/1996 | Ishiguro et al. .............. 600/398 |
| 5,830,139 A | * | 11/1998 | Abreu ........................ 600/405 |

FOREIGN PATENT DOCUMENTS

| | | |
|---|---|---|
| WO | WO 00/71982 A1 | 11/2000 |
| WO | WO 01/05299 A1 | 1/2001 |

OTHER PUBLICATIONS

E.S. Perkins, et al. "A New Recording Tonometer", Trans. Ophthao. Soc. UK; (1977), 97, 679.
E.S. Perkins, "The Ocular Pulse and Intraocular Pressure as a Test for Carotid Artery Stenosis", British Journal of Ophtalmology, (1985), 69, 676–680.
E. Linner, et al., "Die Möglichkeit der flächenunabhängigen Tonometrie", Klim. Mbl. Augenheilk, (1987), 190, 30–33.
E. S. Perkins, "The Ocular Pulse", Current Eye Research, vol. 1 No. 1 (1981) 19–23.

* cited by examiner

Primary Examiner—Charles Marmor
(74) Attorney, Agent, or Firm—Birch, Stewart, Kolasch & Birch, LLP

(57) ABSTRACT

The device (1) for measuring intraocular pressure, in particular a tonometer, has a base body (3) which has a contact surface (5; 17; 30) to be applied to the eye surface. The contour of the contact surface (5) is adapted with a certain tolerance to a standard surface of a standard eye with predetermined internal pressure. Arranged in the contact surface (5) there is a pressure-sensitive unit (7) whose contact surface (9; 23; 31) merges into the contour of the contact surface (5) of the base body (3).

With the device according to the invention, the pressure actually prevailing in the eye can be precisely measured.

20 Claims, 3 Drawing Sheets

DEVICE FOR MEASURING INTRAOCULAR PRESSURE, IN PARTICULAR A TONOMETER

TECHNICAL FIELD

The invention relates to a device for measuring intraocular pressure, in particular a tonometer.

DISCLOSURE OF THE INVENTION

OBJECT OF THE INVENTION

The object of the invention is to make available a device for noninvasive determination of intraocular pressure, with which device the actual pressure prevailing in the eye is measured as precisely as possible.

SOLUTION OF THE OBJECT

The object is achieved by the fact that, in contrast to the known tonometers, the contact surface of a base body to be applied to the eye surface is adapted to fit snugly, with a certain amount of tolerance, onto the contour of a standard surface of a standard eye with predetermined internal pressure, and a pressure-sensitive unit is active within the contact surface. That is to say that the invention, in contrast to the known tonometers, no longer involves generating a small plane measurement surface (applanation area) on the cornea.

In this way, a method is obtained for the first time for direct continuous and noninvasive measurement of intraocular pressure.

Direct measurement: A direct measurement is to be understood as meaning a pressure measurement which takes place without "intermediate measurement" of another physical parameter from which, as this is in functional relationship with the intraocular pressure, said intraocular pressure is only then determined.

Continuous measurement: The pressure changing over time in the eye can be recorded continuously, that is to say as it actually changes.

Noninvasive measurement: The measurement method is noninvasive, it measures without damage through the outer covering of the eye.

In ophthalmology, tonometers had hitherto only been used in indirect measurement procedures. Tonometers developed by Schiötz, Goldmann, Perkins, Dräger and Mackay-Marg can be described as force tonometers; they determined the intraocular pressure by applying a force which deformed the cornea. In the Schiötz tonometer, the depth of the indentation (inward curving) of the cornea was measured under constant force. In the other methods mentioned above, the force needed for applanation (flattening) of the cornea in a defined area was measured. In principle, the tonometers referred to as air-puff tonometers can also be included in the group of force tonometers. With these, the deformation of the cornea generated by the force of impact of an air stream was measured optically. In other words, in these tonometers too the intraocular pressure was determined via "intermediate measurement" of a force.

With the known tonometers cited above, the intraocular pressure could only be measured statically. Each measurement recorded a brief moment in the changing course of the intraocular pressure over time.

Pneumatic tonometers used a further indirect measurement method, but one which permitted continuous measurement. To carry out measurement, the plane exit of a tube through which air flowed was placed on the cornea. The pressure in the tube was regulated in such a way that a constant mass flow of air flowed through the tube and along the cornea. The intraocular pressure was then calculated from the pressure in the tube.

Direct and continuous measurement of intraocular pressure was hitherto possible with invasive methods involving cannulation of the eye.

Direct, continuous and noninvasive methods of measuring intraocular pressure using plane measurement surfaces are described in the following publications:

E. S. Perkins, J. Edwards, R. C. Saxena: "A new recording tonometer", Trans. Ophthal. Soc. UK; (1977), 97, 679, E. S. Perkins: "The ocular pulse and intraocular pressure as a test for carotid artery stenosis", British Journal of Ophthalmology, (1985), 69, 676–680, E. Linner, E. Rumberger, J. Draeger: "Die Möglichkeit der flächenunabhängigen Tonometrie", Klim. Mbl. Augenheilk, (1987), 190, 30–33.

Measurements also with different applanation diameters, compared to measurements by other methods, e.g. on enucleated eyes using intraocular sensors, generally revealed a marked overestimation of the intraocular pressure. It has not hitherto been possible to explain this phenomenon.

In a tonometer developed by Robert (U.S. Pat. No. 5,032,020, EPA 0,327,693, CH-A-673 760), a plane measurement surface was arranged at the center of a lens which lay on the cornea. Despite the improvements which it involved, this tonometer too showed overestimation of the intraocular pressure in some eyes.

The device according to the invention now departs from the path of indentation or applanation of the cornea and uses contour adaptation. The contour of the cornea is adapted by the device to the shape which it adopts when the pressure on both sides of the cornea is equal.

The invention starts from the premise that the cornea of the human eye has a natural radius of curvature which changes only insignificantly as a function of the intraocular pressure and is also maintained at zero intraocular pressure, that is to say the same pressure on both sides of the cornea. The underlying concept of the invention will be explained with reference to an eye Au, as is shown in FIG. 8, which is unaffected by and free from external forces. In the eye Au there is an intraocular pressure P which is to be measured. This internal pressure generates forces $F_r$ which act radially on the cornea H and cause tangential stress $\sigma_t$ therein.

In a next step of the concept, it is assumed that, by applying the contact surface Af, the forces $F_r$ generated by the intraocular pressure and directed radially outward are conveyed directly into the contact surface Af and thus eliminated from the cornea, as is shown in FIG. 9. The area on which the contact surface Af lies is called the contour adaptation area Ka. In the area Ka, the contour of the cornea H adapts to that of the contact surface Af. The contour of the contact surface Af thus determines the deformation of the cornea H. Outside this area Ka, the radial forces $F_r$ of the intraocular pressure still act on the cornea H. The tangential stresses $\sigma_t$ arising as a result of the radial forces $F_r$ continue into the area Ka. If the area Ka is small, then, in the ideal case, only the tangential stresses $\sigma_t$ still prevail here, but no radial forces $F_r$. The radial forces $F_r$ representing the intraocular pressure are thus transmitted without change in the area Ka to the contact surface Af. In the absence of radial forces $F_r$, the tangential stresses $\sigma_t$ change the natural curvature of the cornea H toward greater radii. Accordingly, for an exact intraocular pressure measurement in a small contour adaptation area Ka and with the slightest possible change in the intraocular pressure, no applanation is performed, and instead a positive fit is obtained by the above-defined deformation of the cornea (which it was not possible to do with known tonometers).

The structure of the cornea H is in several layers and consists of the epithelium, Bowman's membrane, the stroma, Descemet's membrane and the endothelium. The deformation described above can be optimized either empirically by measurement series (as will be described below) or by model-based calculations, although, since the complex structure of the cornea H is difficult to model, the latter method is associated with considerable uncertainty.

According to the invention, a contact surface is now used which corresponds to the natural curvature of the cornea in the specifically deformed state. Specifically deformed is understood to signify the state of the cornea H into which it passes when the radial force components $F_r$ are eliminated in a small area; the tangential stresses $\sigma_t$ in this area by contrast are substantially maintained, as has already been explained above. This is achieved by applying the contact surface Af onto the cornea H, whose surface contour is adapted, with a certain tolerance, to the standard surface of a standard eye. Standard surface and standard eye correspond to the properties and dimensions of the average human eye. Measurements have in fact shown that the dimensions of human eyes differ only insignificantly from one another. Slightly greater differences occur only after refractive surgery of the cornea (e.g. by scalpel or laser) has been performed on the eye.

The contact surface is preferably designed as the surface of a base body. Arranged generally at the center of the contact surface there is a pressure-sensitive unit whose contact surface merges into the contour of the contact surface of the base body with a transition tolerance. The transition tolerance should be chosen such that there are no abrupt changes and the surface line of the contact surface of the base body and of the pressure-sensitive unit can be described by one and the same mathematical equation. The simplest contours merging one into the other are contours with one and the same radius of curvature, starting from one and the same center (spherical contour); however, aspherical contours are also possible.

Such a transition tolerance is the ideal case, which in practice can be achieved only with great effort. A depth offset of one millimeter and an angle offset of the curve tangents at the edge of the transition of 10° can be tolerated. However, an offset of 0 micrometer and an angle offset of 0° should be aimed for.

The difference in the radii of curvature between the contact surface and the standard surface set by the defined deformation is so slight that a sufficiently large contour adaptation area is generally obtained even at zero application force through the action of the capillary pressure of the lacrimal fluid. The contour adaptation area can in any case also be increased by a force (application force) additionally applied from outside. This is necessary in particular for the special case described below (FIG. 10 "plane"). The way in which the ideal size of this area is to be determined will be explained below. For the difference in the radii of curvature, a predetermined tolerance can be allowed.

The difference is to be chosen such that a gap is formed, which is as narrow as possible but sufficiently large, between contact surface and corneal surface. The narrower the gap, the greater is the acting capillary pressure and the better the "coupling" between cornea and contact surface. However, the larger the gap, the more lacrimal fluid the gap is able to take up. Too much lacrimal fluid would in fact have to be swabbed, which means increased work.

If the tear film extends past the edge of the contact surface, then the radius of curvature of the tear film to air transition is curved outward and the capillary pressure positive, i.e. it has a repelling action between contact surface and cornea. In order then to create a sufficiently large surface area with contour adaptation, a considerable additional bearing force must be applied, which inadmissibly increases the intraocular pressure. (This effect would be analogous to a greater radius of curvature of the contact surface, as is mentioned in the special case). If the "radius of curvature" is greater, then, in order to create a sufficiently large surface area with contour adaptation, an additional bearing force must likewise be applied.

For carrying out measurement on the human eye with the slightest possible change of the intraocular pressure by this measurement, contact surfaces with radii of curvature of between 8 mm and 11 mm are suitable. In experiments, good results for measurement on healthy and surgically unaltered corneas with different corneal radii of curvature were obtained with contact surfaces having radii of curvature of between R=9.5 mm and R=10.5 mm [see FIG. 10]. In some cases (pathologically and/or surgically altered corneas), other radii of curvature can also be advantageously used.

The contact surface is concave (curved inward). The surface line can be spherical, but also aspherical, as has been mentioned above.

The pressure-sensitive unit can have a membrane whose contour merges as seamlessly as possible into the contour of the contact surface. The reverse of the membrane is acted upon by a pressure-transmitting medium which transmits the pressure to a pressure sensor arranged in the edge area of the base body. An incompressible medium (material) can be used as pressure-transmitting medium. Such a medium is, for example, a fluid, a gel or a flexible pourable compound. These media will preferably be chosen to be transparent in the optical area so that they do not impede viewing through the device onto or into the eye. Since the pressure sensor also lies outside the observation or treatment beam path, it does not cause optical obstruction.

An arrangement with a pressure transmission means can be dispensed with on the one hand if viewing is not required or on the other hand if a small pressure sensor is used which does not appreciably interfere with the optical observation beam path. Such a sensor can be a semiconductor sensor. The sensor can also be electrically coupled to a processing chip. This then permits for example a passive telemetric transmission of the recorded intraocular pressure values (course), preferably over a predetermined period of time. The pressure-sensitive unit preferably has a surface which is adapted to the contour of the contact surface and which merges into the contour of the contact surface with a transition tolerance.

The whole measurement device can also be made so small that it can be worn on the eye almost as a "contact lens" on the eye. This "contact lens" is then held via the lacrimal fluid and "drawn" onto the eye surface with "contour adaptation". The lens surface directed away from the contact surface can then be designed according to the visual acuity required for the patient or for an imaging system of a slit-lamp microscope or another viewing apparatus.

However, the base body can also be made transparent and neutral with respect to imaging.

The contact surface with active pressure-sensitive unit must be applied to the cornea for measuring the ocular pressure. The cornea is generally covered with a tear film. Some of this tear film can remain adhering to the contact surface and would be transferred to another eye in a subsequent measurement, which could lead to infection. It is therefore proposed to use a sterile attachment which is either discarded after the measurement or can be sterilized. The attachment is designed in such a way that material coming to lie over the pressure-sensitive unit is made thin to an extent that, although stability against tearing is afforded, the pressure can nevertheless be transmitted without loss from the cornea to the pressure-sensitive unit (9) during contact.

As has already been explained, the fit of the contact surface is obtained at least in part by capillary forces. The quantity of available lacrimal fluid plays a crucial role in capillary pressure. It has been stated above that too much lacrimal fluid ought to be swabbed away. This awkward swabbing can be eliminated by using a "swab unit". This swab unit is then placed at the edge of the contact surface. The design of this unit will be discussed in greater detail below.

In order to obtain good measurement results, the contact surface should not move in relation to the eye during the measurement. As the patient's eye has been anesthetized only at the surface, an eye movement could occur at any time, even unintentionally. A means is therefore provided which has a predetermined stiffness and which connects the unit having the contact surface to a fixing site. The stiffness must be chosen such that, with the contact surface applied to the eye, the unit is then able at least to go along with small movements of the eye.

BRIEF DESCRIPTION OF THE FIGURES

Examples of the device according to the invention for measuring intraocular pressure are explained in greater detail below with reference to the attached drawings. Further advantages of the invention are evident from the text of the description. In the drawings.

EMBODIMENTS OF THE INVENTION

Figure 1:
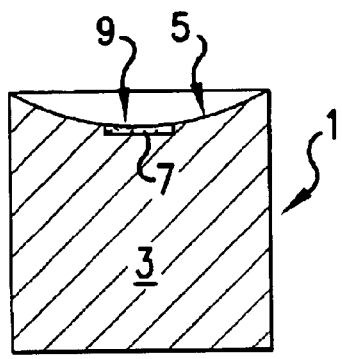
FIG. 1 shows a cross section through the device according to the invention.

The device 1 shown in FIG. 1 for measuring intraocular pressure has a base body 3 which has a contact surface 5 to be applied to the eye surface. The contour of the contact surface 5 is adapted, with a certain tolerance, to the standard surface of a standard eye with predetermined internal pressure. It will be noted here, for clarity, that the radius of curvature of the natural eye changes only very slightly as a function of the intraocular pressure. A standard surface of a naked eye is typically assumed to have a radius of curvature of 7.7 mm as a result of the internal pressure. The radius of curvature of the concave (inwardly curved) contact surface 5 lies typically between 8 mm and 11 mm, preferably between 9.5 mm and 10.5 mm. As has already been stated above, the contact surface 5 can be made spherical or alternatively also aspherical.

A pressure-sensitive unit, e.g. a pressure sensor 7, is active in the contact surface 5, which is in this case for example of centric design. A semiconductor sensor will preferably be used as pressure sensor 7, e.g. on account of the small dimensions and minimal weight. The pressure sensor 7 can be connected via signal lines (not shown) to an external processing circuit (not shown). Preferably, however, a processing chip is integrated directly in the pressure sensor 7. The processing chip should then be designed for example in such a way that a passive telemetric transmission to a remote evaluation unit (not shown) is possible. The surface 9 of the pressure sensor 7 or of the integrated unit (pressure sensor+processing chip) merges seamlessly into the surface contour of the contact surface 5.

Figure 10:
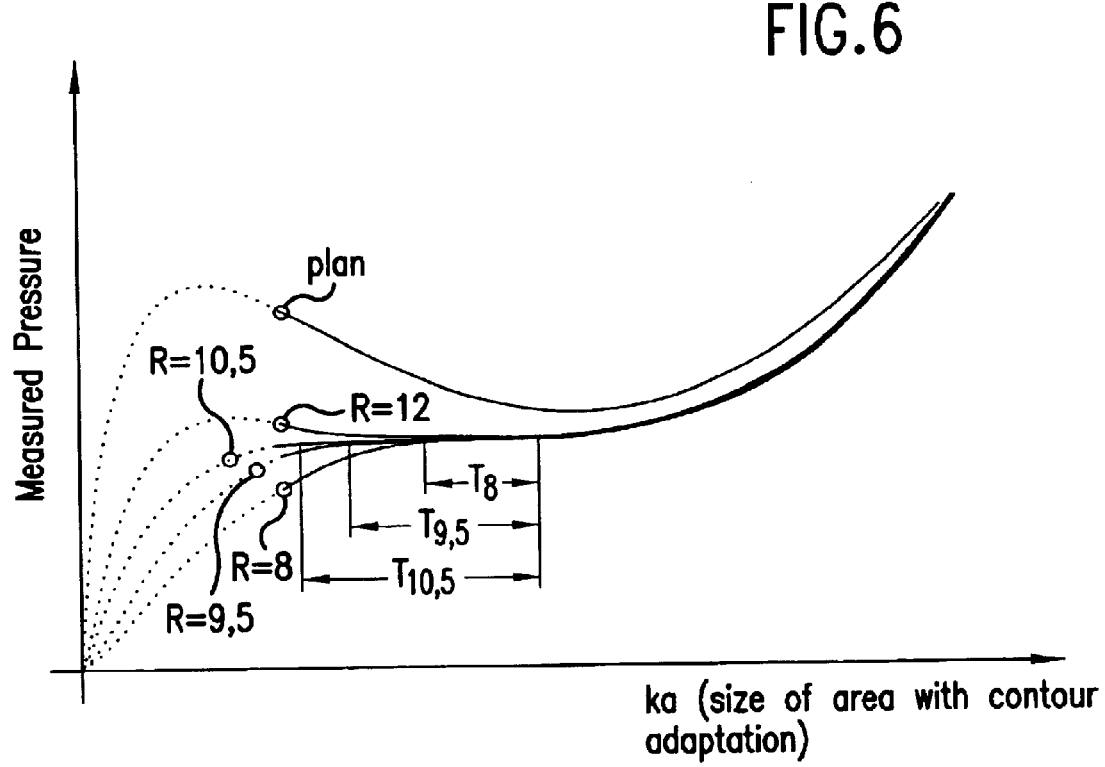
FIG. 10 shows a measurement diagram for determining the optimum contour (the radius of curvature R is the parameter) of the contact surface of the device according to the invention.
Figure 8:
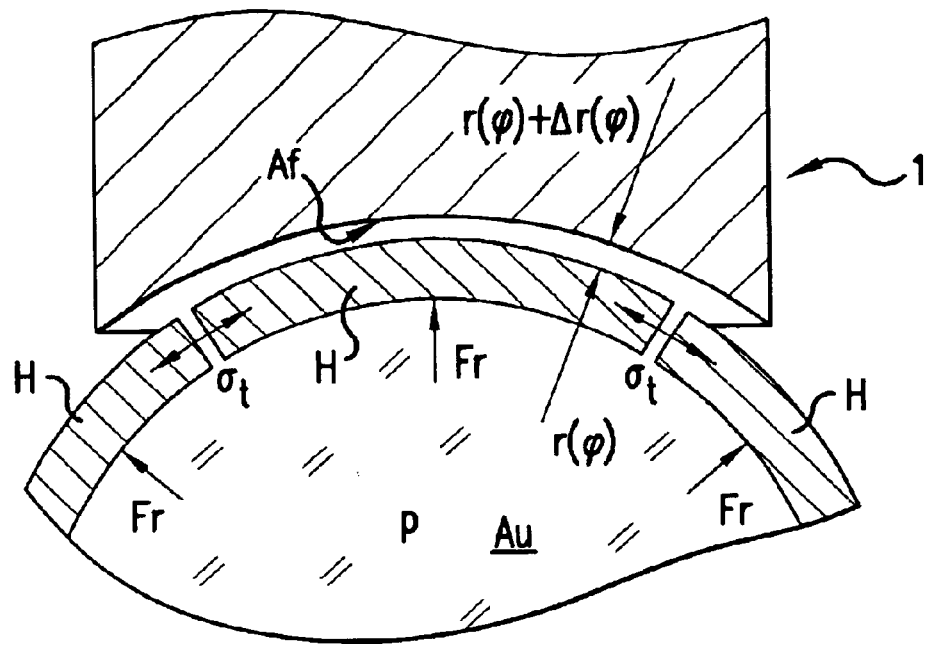
FIG. 8 shows a schematic representation to explain the forces and stresses acting in and on the cornea as a result of the intraocular pressure.
Figure 9:
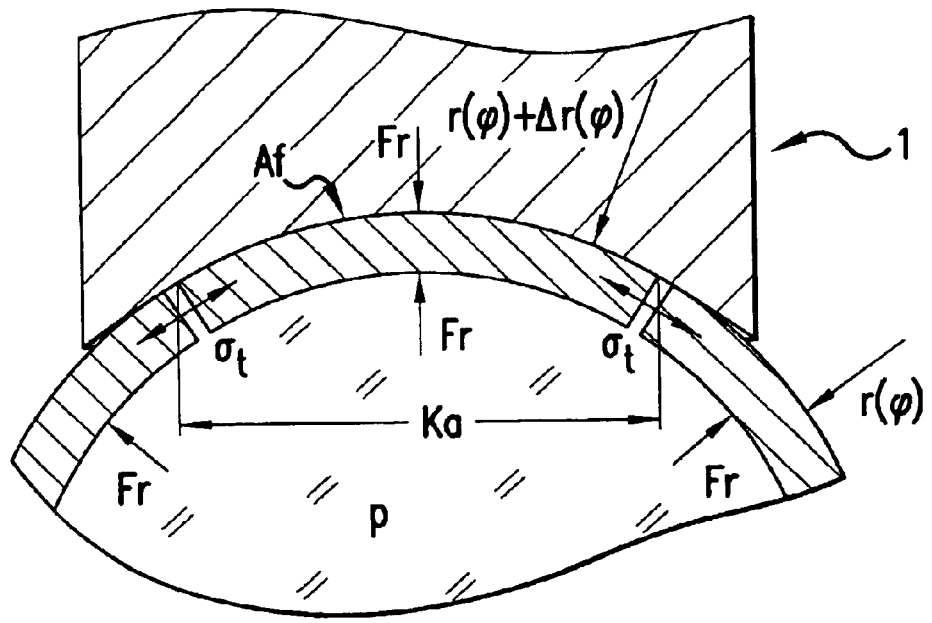
FIG. 9 shows an analogous representation to that in FIG. 8, with the device according to the invention applied.

In order to ensure, for measurement with the least possible change in the intraocular pressure, that the cornea H at the center of the contact surface 5, that is to say where the pressure sensor 7 sits, ideally has only tangential stresses $\sigma_t$ and no longer any radial forces $F_r$, the contact surface 5, in the state when applied to the eye, must have a radius of curvature of $r(\phi)+\Delta r(\phi)$, where r is the distance of a surface point on the contact surface Af from the center point of the eye, and $\phi$ is the angle by which the point deviates from the optic axis. Here, we assume a spherical eye model with symmetry to the optic axis, which does not correspond to reality but which for these explanations can be ignored. With contour adaptation, a certain volume in the eye is displaced, which would lead to a pressure increase in the eye and as a result to a measurement error. Except in the special case discussed below, this volume should be as small as possible. At most, it should be as great as in a standard Goldmann examination and thus smaller than 0.58 mm³. For the above mentioned radii of curvature of the contact surface 5 of between 9.5 mm and 10.5 mm, a diameter of the contour adaptation area of 4 mm is sufficient. The displaced volume in an eye pressure measurement is then between 0.38 mm³ and 0.51 mm³. At greater radii of curvature, the displaced volume is greater and the pressure increase caused by this leads to measurement errors. In FIG. 10, at a radius of curvature of 12 mm, it is already evident that the calibration curve is never flat. In other words, the pressure across the whole area is dependent on the size of the surface area with contour adaptation Ka. With a plane contact surface (FIG. 10), this is even more pronounced.

If the abovementioned conditions are met in the area of the pressure sensor 7 for a cornea free from radial force components $F_r$, a real intraocular pressure is measured. That is to say, all the forces acting on the pressure sensor 7 act perpendicular to its surface. Like conventional pressure sensors, the pressure sensor 7 can be acted upon with a calibrated pressure of a gas or a fluid for calibration purposes.

To determine the ideal radius of curvature required for a measurement and also an associated optimum size of the contact surface 5, the procedure set out here is followed. A calibration curve is taken, as is shown in FIG. 10. In this calibration curve, the measured pressure is shown as a function of the size of the surface area Ka with contour adaptation, at different contours of the contact surface with the radius of curvature R of the contact surface as parameter. For error-minimized measurement, a radius of curvature must be chosen in which the curve in FIG. 10 extends flat in as large an area as possible. That is to say, in which the device measures the same pressure. The tolerance values for the surface areas with contour adaptation, within which the device measures the unchanged intraocular pressure, are identified by T, where the index indicates the respective associated radius of curvature R of the contact surface. The absence of an indication $T_{12}$ and $T_{plan}$ shows that in no area do these curves extend parallel to the "Ka axis" and they are therefore unsuitable for measuring the intraocular pressure of the human eye without alteration of the intraocular pressure. Exceptions to this are, for example, the special cases discussed below in which a change in the intraocular pressure is permitted or desired, in order to be able to measure the "artificial" intraocular pressure.

Compared to what has been explained above, greater differences in the radius of curvature between the cornea and the contact surface can also be chosen, which can be an advantage in special cases of use. For example, the radius of curvature can be infinite, which corresponds to a plane surface. In the case of a convexly shaped surface, it is negative. In both these cases, it is therefore necessary to work with considerably greater contour adaptation areas. For example, measurement of the intraocular pressure can be performed with the cornea deformed flat when cutting flaps during LASIK treatment. In such measurements, the intraocular pressure is substantially increased by the large volume displacement in the eye, which is even desirable for example in the case of LASIK treatment. Referring to the calibration curve in FIG. 10, it is not evident, for these conditions, what size the surface area of the contour adaptation must have to ensure that the altered intraocular pressure is exactly determined. Experiments have shown that a minimum size of 5 to 6 mm is necessary. The maximum size results indirectly from the permissible pressure in the eye of 100 to 150 mmHg.

The device 1 is an economical construction which preferably only serves for measuring pressure. For cost reasons, no value will be placed here on good optical transmission, e.g. for observation purposes, in the eye. However, good optical transparency of the device can of course be achieved without any problem, if so desired. The base body 3 can thus consist of a nontransparent material. The device 1 is generally used together with a so-called slit lamp and is held in the operator's hand and pressed against the patient's eye. The device 1 can also be mounted on a slit lamp and the adjustment means of the latter is then used to move the device onto the eye. However, the device 1 can also contain its own adjustment means and force applicator (application force) and can be applied to the eye in conjunction with the slit lamp.

The device can also include its own adjustment means, a force actuator and an observation unit and can then be applied to the eye independently of a slit lamp.

Figure 2:
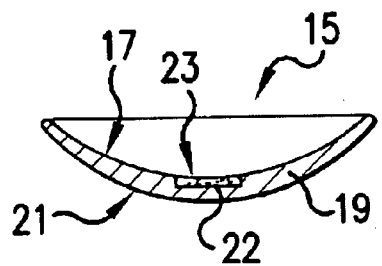
FIG. 2 shows a cross section through a variant of the device shown in FIG. 1.

FIG. 2 shows a variant of the device 1. The device 15 shown in FIG. 2 is designed in the form of a contact lens. It too has a contact surface 17 whose contour is adapted to the standard surface of a standard eye with a certain tolerance, as was described above. The base body 19 of the device 15 is made of transparent material and corresponds substantially to that of "soft" or "hard" contact lenses. The surface 21 directed away from the contact surface 17 is designed according to optical criteria for the visual correction to be obtained for the patient in question. If no correction is necessary, an optically neutral contact lens is used. The force for obtaining the fit between "contact lens" and cornea is applied via the capillary pressure of the tear film. The arrangement of the pressure sensor 22 is also analogous to the arrangement in the device 1. That is to say the surface 23 of the pressure sensor 22 merges (as far as possible) seamlessly into the contact surface 17.

Figure 3:
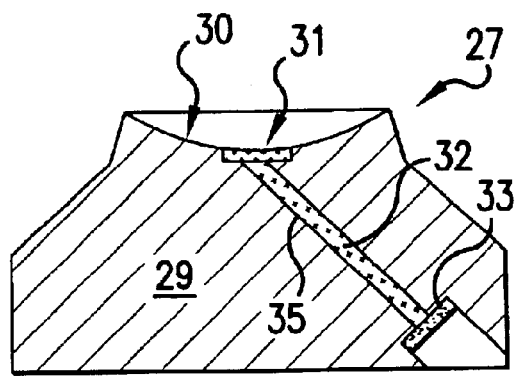
FIG. 3 shows a cross section through a further variant of the devices shown in FIGS. 1 and 2.

FIG. 3 shows a further variant of a measurement device 27 compared to the devices shown in FIGS. 1 and 2. The device 27 has a preferably transparent base body 29. The contact surface 30 is of analogous design to the contact surfaces 5 and 17. A pressure-sensitive unit in this case has a membrane 31 in the contact surface 30, a pressure-transmitting medium 32 and a pressure sensor 33 arranged in the edge area of the base body 29. The curve of the membrane 31 merges seamlessly into the contour of the contact surface 30. The pressure-transmitting medium 32 is incompressible, e.g. a fluid, a gel or a flexible pourable compound. The medium 32 is enclosed in a cavity system 35. Any volume expansions can be compensated for example in the manner described in WO 00/71982. The medium 32 and the base body 29 will preferably be made transparent for optical radiation in order to be able to view the eye through the device 27. The refractive power of the medium 32 and of the material of the base body 29 will also preferably be chosen so as to be approximately equal. The width of the base body 29 is greater than that of the base body 3 in order to obtain a greater viewing angle.

Figure 4:
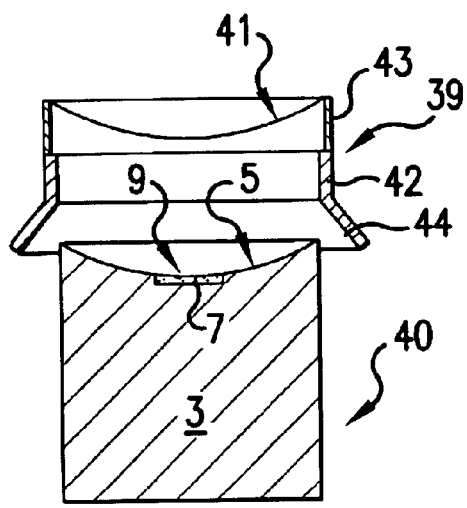
FIG. 4 shows an alternative embodiment with removable sterile attachment.

FIG. 4 shows a device 40 for intraocular pressure measurement analogous to the device shown in FIG. 1. In contrast to the embodiment in FIG. 1, a removable attachment 39 is provided here. This attachment 39 is sterile and is taken from a sterile package (not shown). For the eye examination, it is then fitted onto a base body 3 which is identical to that one of the device 1 in FIG. 1. In a particular embodiment, this attachment 39 is made sterilizable, so that it can be used for further examinations after being sterilized. However, the attachment 39 will generally be designed as an economical disposable element. The expensive pressure sensor 7 still remains in the base body 3 and is covered by the attachment 39 during the intraocular pressure measurement.

The attachment 39 is designed in such a way that it can be fitted onto the base body 3 (device 1) in a detachable manner. Starting from a circular cylindrical cross section of the base body 3, the attachment 39 too is of circular cylindrical design in its inner contours and thus also its outer contours. The attachment 39 has a frame whose internal diameter is greater than the external diameter of the base body 3 of the device body 3 by a clamping tolerance. At the top, the attachment 39 is closed off by a thin membrane 41. The membrane 41 can be made of plastic or metal. Its surface contour corresponds to that of the contact surface 5. The transition from the frame 42 to the membrane 41 is via an edge thickening 43. The thickening 43 increases the stability of the attachment 39 and makes it easier to fit the membrane 41. Arranged on the circular cylindrical frame 42, toward the bottom in FIG. 4, there is an outwardly projecting annular collar. The collar 44 is intended on the one hand to facilitate handling and additionally to prevent any lacrimal fluid from dropping onto the base body 3.

To fit the attachment 39 onto the base body 3, attachment 39 and base body 3 are held in the position shown in FIG.

4. A few drops of a sterile fluid are placed on the contact surface 5 and the attachment 39 is then pressed on. A small interspace between contact surface 5 and the reverse of the membrane is completely filled with the fluid. Excess fluid is displaced toward the thickening 43 upon fitting. A perfect transmission of force to the pressure sensor 7 through the thin fluid film is obtained.

Instead of a sterile fluid, a sterile gel can also be used. It is possible to dispense with fluid and gel if the touching surfaces have corresponding properties [sufficient adhesion (electrostatic, capillary action, etc.)].

The base body 3 and the attachment 39 which can be placed on it do not have to have a circular cylindrical design; other cross sections are possible.

Figure 5:
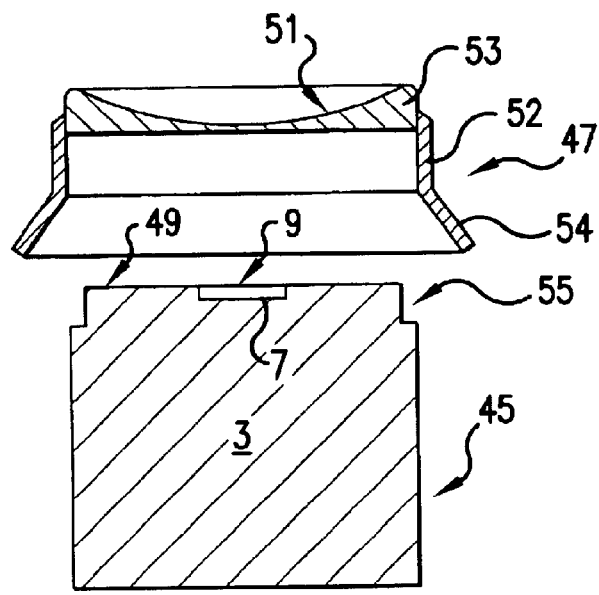
FIG. 5 shows an alternative embodiment of the embodiment shown in FIG. 4.

A further alternative embodiment 45 is shown in FIG. 5. Here too, analogously to the alternative in FIG. 4, there is a base body 3 and an attachable sterile attachment 47. Here too, the attachment 47 has a circular cylindrical frame 52 and a collar 54 which is designed analogously to the collar 44. In contrast to the embodiment in FIG. 4, however, the pressure sensor 7 is here fitted into a plane surface 49. This plane surface 49 can be made more economically than the curved surface 5 of the base body 3. However, in contrast to the membrane 41 of the attachment 39, the attachment 47 has a body 53 of flexible material onto which a contact surface 51 is molded. In its area coming to lie over the pressure sensor, the flexible body 53 has an extremely thin wall thickness. The thinner the better. The minimum wall thickness is determined only by mechanical requirements against tearing. On account of the extremely thin wall thickness above the pressure sensor 7, the pressure is taken by the contact surface 51 from the eye and conveyed without loss to the pressure sensor 7. This is exactly the case when the pressure required to displace a flexible material of the body 53 from the area with contour adaptation into the area without contour adaptation is much greater than the pressure which has arisen in the contour adaptation.

Here too, analogously to the embodiment in FIG. 4, a sterile fluid or a sterile gel is placed on the plane surface 49 during fitting. Excess fluid or excess gel is displaced into a ledge 55 during fitting. Here too, as in the above embodiments, it is possible to dispense with fluid and gel.

The contact surface 51 can be provided with a coating or covered with a membrane. In this way, for example good wetting by the tear film can be achieved. By this measure, the surface properties can be favorably influenced to provide a simple and reproducible measurement.

The attachments 39 and 47 described above can also be designed in such a way that they can be fitted onto the base body 29, as is represented in FIG. 3.

The contact surface 5, 30, 41 and 51 should as far as possible not slide on the eye surface, because this causes disruptive spikes in the measurement signal. That is to say, a construction should be found in which the contact surface or the unit with the contact surface also moves along with at least small movements of the eye (approximately ±1 mm). Such requirements can be satisfied with a unit which is suspended in a flexible ("wobbly") manner but has a predetermined stiffness. However, the connecting means 62 to the unit must still be stable enough to ensure that there is no downward sagging.

Figure 6:
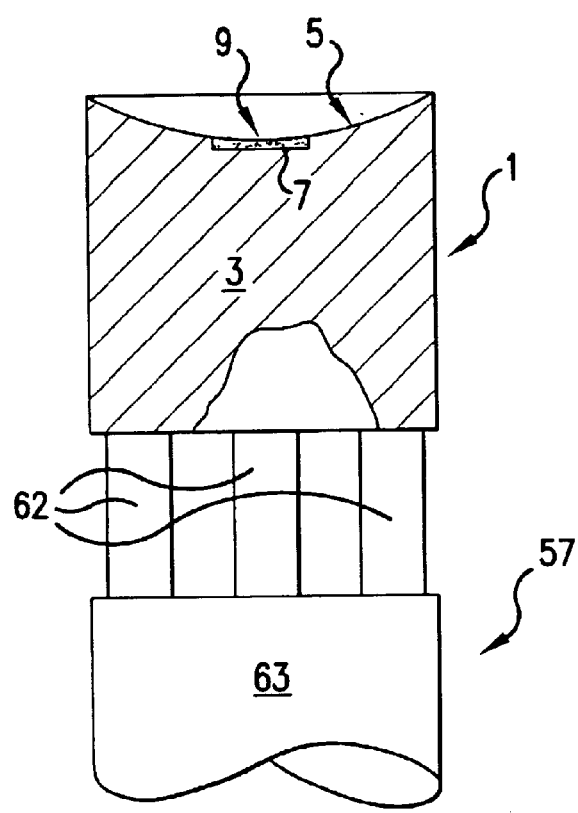
FIG. 6 shows an alternative embodiment with an elastic fixture.

Such a measurement device is shown in FIG. 6 as including a device 1 connected to a flexible holder 57, consisting of flexible supports 62 and grip element 63. The device 1 is connected via three flexible supports 62 as connecting means to the grip element 63 serving as fixing site. In addition to the grip element 63, it is possible also to use other fixing means such as stands, mounts, etc. The flexible supports can consist of metal foil, rubber, silicone or other flexible materials. Instead of the device 1, the devices shown in FIGS. 3, 4 and 5 can of course also be held flexibly.

Figure 7:
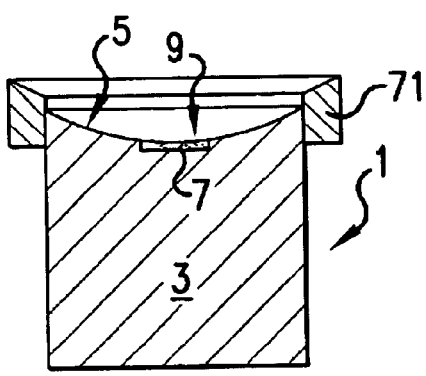
FIG. 7 shows an alternative embodiment with a swab unit for taking up excess lacrimal fluid.

If an eye produces too much lacrimal fluid, this can be reduced by a measure shown in FIG. 7. A swab unit 71 adapted to the cross section and shape of the devices 1, 27, 40 or 45, in this case circular, is mounted on the device shown in FIG. 1. The swab unit 71 consists of a hygroscopic, soft and flexible material. This material is such that within the first few seconds of being placed on the eye it can take up a defined quantity of approximately 100 $\mu$l of lacrimal fluid. Moreover, the swab unit 71 must not damage the cornea and must adapt to the contour of the cornea with a slight force application. The material used can, for example, be a self-deploying sponge or a cellulose.

In contrast to the configuration in FIG. 7, the swab unit can also be designed as part of the contact surface. If a large volume is required to be taken up, the swab unit can also be designed so as to come to lie in the two lid slits.

The swab units can also be arranged analogously to FIGS. 3 to 6.

The advantage of the above-described devices according to the invention lies in the fact that, compared to the known tonometers, it is not a plane surface that is used, but instead a contour adapted to the cornea, as a result of which the cornea is in a state substantially free from radial force components, thus permitting an intraocular pressure measurement which is independent of the mechanical properties of the cornea and with reduced measurement errors. Known tonometers generally performed a static measurement; dynamically changing parameters could not be determined.

With the device according to the invention, dynamic parameters can preferably also be determined. In addition to long-term variations in the intraocular pressure depending on the time of day or the activity of the person in question, the intraocular pressure can also be determined on a short-term basis as a function of pulse rate and emotional influences. The time course of the intraocular pressure permits a wide range of medical conclusions, and these are not limited to ophthalmology alone.

The ocular fundus can be closely examined using special alternative embodiments of the device according to the invention. This advantageous viewing of the ocular fundus together with a measurement of the intraocular pressure is described in EP-B-0,327,693. However, compared to the device used there, the device according to the invention is much easier to use and gives more accurate measurement results.

What is claimed is:

1. Device for measuring intraocular pressure, comprising:
    a base body comprising
        a contact surface adapted to be applied to an eye surface of an eye-wall, said eye having said intraocular pressure, the contour of said contact surface is substantially a contour of a standard surface of a standard eye, and
        a pressure-sensitive unit having a curved contour adapted to said contour of said standard surface of said standard eye,
    said pressure-sensitive unit sensing intraocular pressure on said contact surface while said eye surface is adapted to said contour of said contact surface,
    wherein
        said contour is defined as a shape at which a pressure on an inside of said eye-wall and a pressure on an outside of said eye-wall are equal in the region of the contact surface.

2. Device according to claim 1, further comprising a membrane which is adapted to the contour of the standard surface and makes up at least a partial area of the contact surface, said membrane having a reverse face, the reverse face of the membrane cooperating with the pressure-sensitive unit arranged in the base body.

3. Device according to claim 2, wherein said pressure sensitive unit has a pressure sensor, the reverse face of the membrane being acted upon by a pressure-transmitting medium which transmits the pressure to said pressure sensor.

4. Device according to claim 3, wherein said base body has edge areas, said pressure sensor being in connection with said pressure-transmitting medium and being arranged in one of the edge areas.

5. Device according to claim 3, wherein said pressure-transmitting medium is incompressible.

6. Device according to claim 3, wherein said pressure-transmitting medium is a fluid.

7. Device according to claim 3, wherein said pressure-transmitting medium is a transparent fluid.

8. Device according to claim 3, wherein said pressure-transmitting medium is a flexible pourable compound.

9. Device according to claim 3, wherein said pressure-transmitting medium is a flexible, transparent pourable compound.

10. Device according to claim 1, wherein a surface of said pressure-sensitive unit merges into the contour of the contact surface with a transition tolerance.

11. Device according to claim 1, wherein said base body comprises a curved surface which lies opposite the contact surface and which produces a lens effect for at least one of viewing or treating the eye surface or ocular fundus and to change the patient's vision.

12. Device according to claim 1, wherein said base body has a weight and dimensions and a reverse, the weight, dimensions and reverse are designed in such a way, that the base body is adapted to be worn as a vision-correcting element on a patient's eye.

13. Device according to claim 1, wherein the base body is made optically transparent, said base body having a refractive power and being situated in an observation beam path, said base body having surfaces lying in said observation beam paths, said surfaces being designed in such a way that, together with the refractive power of the eye, said surfaces together with the refractive power of the base body generate an optical neutral image.

14. Device according to claim 1, further comprising an attachment, said attachment being exchangeable and having an attachment-contact-surface adapted to be placed between said cornea and said contact surface with said pressure-sensitive unit, said attachment-contact-surface being sterile and having a thickness, said thickness being sufficient to prevent tearing and being sufficiently thin such that the pressure from the cornea to the pressure unit is transmitted without loss.

15. Device according to claim 14, wherein said attachment has a case material, which, in an area over the pressure-sensitive unit, is thin to an extent that the case material does not tear, but thin enough such that pressure transmitted from the cornea is sensed by the pressure-sensitive unit.

16. Device according to claim 1, further comprising an attachable, exchangeable swab unit which is arranged at the edge of the contact surface and which is adapted to take up and remove excess lacrimal fluid from the area of the contact surface so that the lacrimal fluid has no effect on the measurement.

17. Device according to claim 1, further comprising a means which has a predetermined stiffness and which connects a unit of the base body with contact surface to a fixing site, the stiffness being chosen in such a way that, with the contact surface applied to the eye, the unit also moves along with at least small movements of the eye.

18. Device according to claim 1, wherein said base body has a transparent area adapted to allow a user to see into or onto the eye.

19. Device according to claim 1, wherein said base body comprises an aspherically curved surface which lies opposite the contact surface and which produces a lens effect for at least one of viewing or treating the eye surface or ocular fundus and serving to change the patient's vision.

20. Device according to claim 1, wherein said device for measuring intraocular pressure is a tonometer.

* * * * *

UNITED STATES PATENT AND TRADEMARK OFFICE
CERTIFICATE OF CORRECTION

PATENT NO. : 6,893,398 B2
DATED : May 17, 2005
INVENTOR(S) : Hartmut Kanngiesser It is certified that error appears in the above-identified patent and that said Letters Patent is hereby corrected as shown below:

<u>Title page,</u>
Item [73], Assignee: "ODC Ophthalmic Development Company AG, Zurick (CH)"
should read
-- SMT Swiss Microtechnology AG
Port, Switzerland --.

Signed and Sealed this

Twenty-eighth Day of March, 2006

JON W. DUDAS
*Director of the United States Patent and Trademark Office*